(12) United States Patent
Martin

(10) Patent No.: US 8,368,895 B2
(45) Date of Patent: Feb. 5, 2013

(54) GAS ANALYSIS ARRANGEMENT

(75) Inventor: Hans Göran Evald Martin, Delsbo (SE)

(73) Assignee: Senseair AB, Delsbo (SE)

( * ) Notice: Subject to any disclaimer, the term of this patent is extended or adjusted under 35 U.S.C. 154(b) by 596 days.

(21) Appl. No.: 11/041,128

(22) Filed: Jan. 21, 2005

(65) Prior Publication Data
US 2005/0180889 A1    Aug. 18, 2005

Related U.S. Application Data

(63) Continuation of application No. PCT/SE03/01235, filed on Jul. 21, 2003.

(51) Int. Cl.
*G01N 21/00* (2006.01)
(52) U.S. Cl. ........................................ 356/437
(58) Field of Classification Search .......... 356/437–440; 250/343
See application file for complete search history.

(56) References Cited

U.S. PATENT DOCUMENTS

| | | | |
|---|---|---|---|
| 3,997,786 A | | 12/1976 | Lauer et al. |
| 4,190,363 A | * | 2/1980 | Adrian ............................. 356/437 |
| 4,228,352 A | | 10/1980 | Adrian |
| 4,557,603 A | | 12/1985 | Oehler et al. |
| 4,829,186 A | * | 5/1989 | McLachlan et al. ............ 356/51 |
| 4,998,022 A | * | 3/1991 | Tregay ............................. 356/136 |
| 5,053,754 A | | 10/1991 | Wong |
| 5,060,508 A | | 10/1991 | Wong |
| 5,170,064 A | | 12/1992 | Howe |
| 5,222,389 A | * | 6/1993 | Wong ............................... 356/437 |
| 5,502,308 A | * | 3/1996 | Wong ............................... 250/343 |
| 5,815,276 A | * | 9/1998 | Fry ................................... 356/437 |
| 5,886,348 A | * | 3/1999 | Lessure et al. .................. 250/343 |
| 5,946,084 A | * | 8/1999 | Kubulins ......................... 356/128 |

(Continued)

FOREIGN PATENT DOCUMENTS

| | | |
|---|---|---|
| GB | 2 262 338 A | 6/1993 |
| JP | 51-136473 | 11/1976 |

(Continued)

OTHER PUBLICATIONS

Notice of Reasons of Rejection with English Language Translation dated Oct. 9, 2009, issued in Japanese patent application No. 2004-522897.

*Primary Examiner* — Gregory J Toatley
*Assistant Examiner* — Juan D Valentin
(74) *Attorney, Agent, or Firm* — Drinker Biddle & Reath LLP

(57) ABSTRACT

The present invention comprises a gas analysis arrangement (1), comprising a chamber (20) containing a sample of gas ("G"), light-emitting means (3), means (4) for receiving light that has been reflected through the chamber, and an electronic circuit (5) for calculation, adapted such that it is able by means of spectral analysis to analyze and determine the presence of a selected gas or mixture of gases present as a sample ("G") of gas within the said chamber (20). The said chamber (20) offers one or several apertures for the passage of the sample of gas into and out of the said chamber. The said chamber (20) is assigned a somewhat curved shape, with at least one concave curved light-reflecting surface (30b) extending between the said light-emitting means (3) and the said light-receiving means (4). The said aperture (30) is located as a narrow continuous extent between the said light-emitting means (3) and the said light-receiving means (4) and that the said aperture (30) is assigned a size and longitudinal extent that offers rapid passive exchange of one sample ("G") of gas within the chamber (20) for another sample of gas.

7 Claims, 3 Drawing Sheets

U.S. PATENT DOCUMENTS

| | | | |
|---|---|---|---|
| 5,973,326 A | 10/1999 | Parry et al. | |
| 6,067,840 A * | 5/2000 | Chelvayohan et al. | 73/23.2 |
| 6,199,257 B1 * | 3/2001 | Munk et al. | 356/440 |
| 6,201,245 B1 | 3/2001 | Schrader | |
| 6,205,272 B1 * | 3/2001 | O'Rourke et al. | 385/33 |
| 6,410,918 B1 * | 6/2002 | Kouznetsov | 250/343 |
| 6,466,323 B1 * | 10/2002 | Anderson et al. | 356/445 |
| 6,527,398 B1 * | 3/2003 | Fetzer | 356/437 |
| 6,690,452 B2 * | 2/2004 | Wilks, Jr. | 356/436 |

FOREIGN PATENT DOCUMENTS

| | | | |
|---|---|---|---|
| JP | 01-097841 | | 4/1989 |
| JP | 5-508929 | | 12/1993 |
| JP | 07-198600 | | 8/1995 |
| WO | WO 93-11418 | | 6/1993 |
| WO | WO 98/09152 | * | 5/1998 |

* cited by examiner

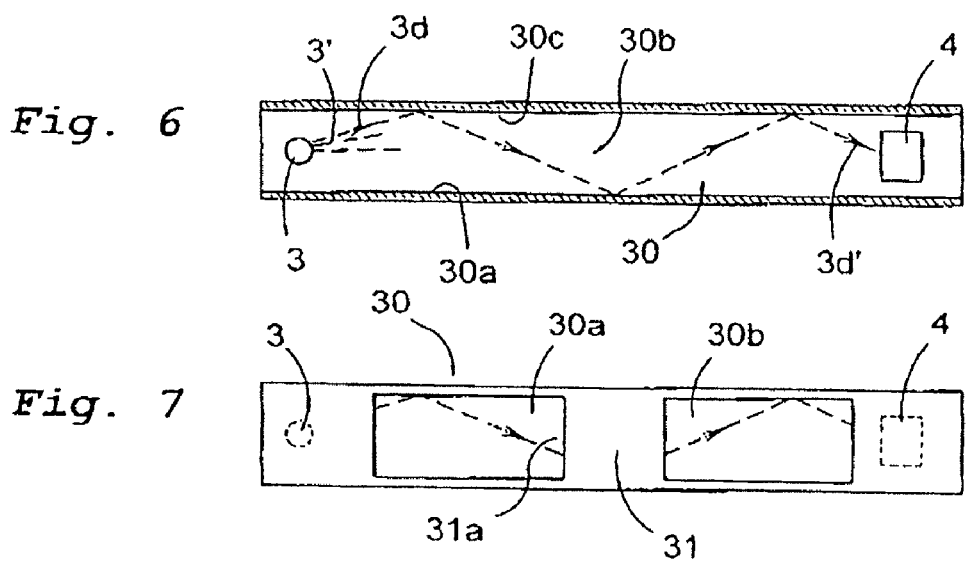
Fig. 6
Fig. 7
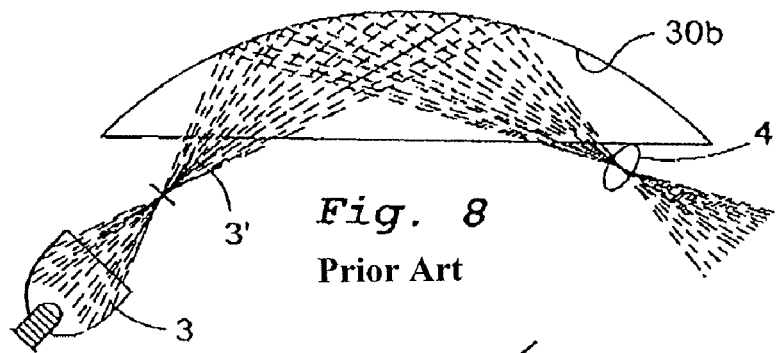
Fig. 8
Prior Art
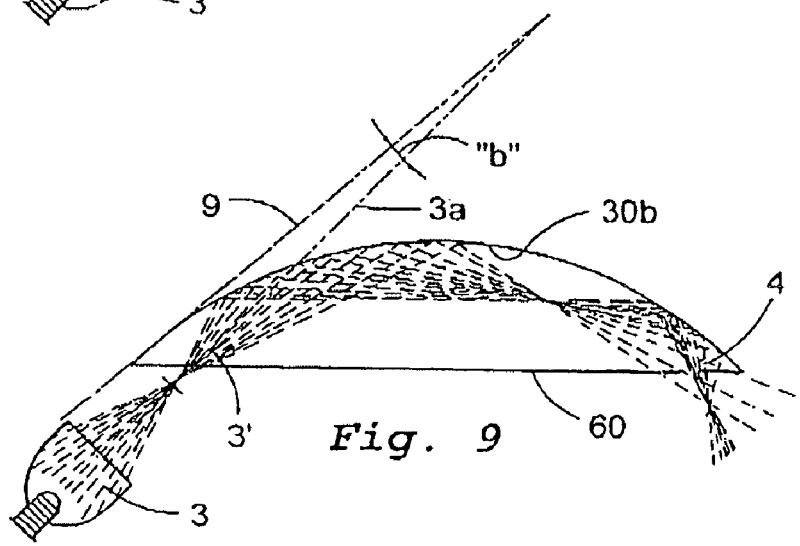
Fig. 9

GAS ANALYSIS ARRANGEMENT

CROSS REFERENCE TO RELATED APPLICATIONS

This application is continuation of International Application No. PCT/SE2003/001235 filed Jul. 21, 2003, which claims priority from Swedish Application No. 0202292-9 filed Jul. 22, 2002.

TECHNICAL FIELD OF THE INVENTION

The present invention relates in general to a gas analysis arrangement, and more particularly to such an arrangement that comprises: a chamber, surrounding or containing a gas sample, light-emitting means, means of receiving light, reflected through the walls of said chamber, and an electronic circuit, where this circuit is adapted such that it is able, among other functions, to analyse, by means of spectral analysis of the received light relative to the emitted light, and in this manner determine the presence of and concentration of a selected gas and/or mixture of gases, if present, occurring at any instant within the said chamber.

Furthermore, the invention is based on the surfaces or walls formed within the chamber, which are to reflect emitted light, such as IR-light (Infra-red light), offering extremely efficient light-reflecting properties.

Furthermore, the arrangement requires that the said chamber is to offer or expose one or several apertures, for the passage of gas samples into and out from the said chamber, usually with the aid of diffusion effect.

In particular, the present invention relates to such gas analysis arrangements that make use of a chamber that can be considered to be designed, formed or assigned a long and narrow inner shape, that is, the total length of the chamber, in order to offer a required light path, adapted to a desired measurement length.

The said aperture and/or apertures are thus to be located adjacent to or next to the chamber and in this way connect the inner space of the chamber with a chamber surrounding gas or mixture of gases, such that changes that occur in the concentration of gas and/or the composition of the gas mixture within the surrounding gas or mixture of gases can, though diffusion, change the concentration of gas and/or the composition of the mixture of gases within the gas sample enclosed by or contained in the chamber.

The said chamber is otherwise limited by a number of interacting wall sections or surfaces that are to be present, as a matter definition, between the said light-emitting means and the said light-receiving means.

BACKGROUND TO THE INVENTION

Methods and arrangements with the features described above are previously known in a number of different embodiments.

For an accurate measurement of the occurrence of a selected gas and/or selected mixture of gases and/or for a careful measurement of the concentration of a gas and/or mixture of gases, there arises a requirement for measurement paths of different lengths, coordinating within the chamber, where one or several such measurement paths are required for a selected gas or mixture of gases, and one or several of the same or different measurement paths is or are required for a second selected gas or mixture of gases.

Thus, the use of a first principle, which will be referred to as Principle (A), is previously known for measurements that require relatively short measurement paths for the associated purpose, related to light reflection of a structure that leads to the concept of wave-guides.

Thus, the use of a second principle, which will be referred to as Principle (B), is also previously known for measurements that require relatively long measurement paths for the associated purpose, related to the use of opposing elliptically shaped mirror surfaces, whereby a light, produced with the form of a point, is allowed to be reflected a number of times between these mirror surfaces, a number of times that has been selected with reference to the desired measurement path, in order in this way to offer an adapted and long measurement path.

It is obvious for one skilled in the arts that even though Principle (B) is intended for an application, according to the pre-conditions specified above, it can also be applied within Principle (A).

The present invention will therefore, for reasons of simplicity, be considered as related principally to Principle (A) described above.

As an example of the prior art, with respect to Principle (A) described above, and of the technical area to which the invention can be considered to be related, the contents of the International Patent document WO 93/11418 (International patent application number PCT/US91/08822) can be mentioned, where FIG. 1 of the said patent publication is also given as FIG. 1 of the present application, for the purposes of illustration, and as an example of technology on which the present invention can be considered to be based.

Here, the use is proposed of a chamber or cell (10), containing a gas sample, adapted such that it can be used for a gas analysis arrangement, that consists of an extended "straight" tube (21) and which has been assigned four, inwardly facing, light-reflecting surfaces (22) assigned to the walls, in order in this way to allow the tube to function as a wave-guide, adapted to lead, not only directly but also following reflection, a somewhat diverging light beam or light cone from a light-emitting means (20) to a detector or light-receiving means (16), with a selected aperture angle and where light rays produced within the light beam are to pass through the contained sample of gas.

In particular, an embodiment is shown here in which a number of penetrating apertures or small holes (24) are applied to the surfaces or the walls of the extended tube (21) and make possible in this manner the slow passage by diffusion of an immediately surrounding gas or mixture of gases into and out from the cell (10).

Particles of smoke and dust, of size greater than 0.1 micrometers, are held outside of the cell (10) by the use of a number of small semi-permeable membranes (28) corresponding in number to the number of apertures, and allowing each one of these to cover one aperture in the tube.

Here is revealed in particular the use of means such that condensation of sample components from the gas can be evaporated by arranging electrical heating of the gas sample that is in the cell to a temperature that lies above the dewpoint temperature of the component that is to be evaluated within the straight tube (21).

In particular, the design is revealed in an embodiment of eighteen (18) diametrically located small holes (24), evenly distributed in four lines along the four sides of the tube and along its complete length, where each hole is provided with one filter. Other embodiments also belong to the prior art, where patent publication U.S. Pat. No. 5,170,064 reveals and describes a gas detector based on infra-red radiation (IR-radiation) that uses a chamber, which has been designed as an elliptical or ellipsoidal reflecting surface.

The ellipsoidal reflecting surface has thus, in a known manner, a first focal point and a second focal point.

One focal point is located within a chamber (4), in order therein to contain an inert gas, and one chamber (3) is adapted to contain the gas sample intended for analysis.

Light-emitting means (24) are here located at one of the focal points (11), and light-receiving means (26) are located at the second focal point (12).

The two chambers or cells (2, 4) are divided from each other by a transparent sheet (15).

Furthermore, the use of detecting means for the selective detection of gases that is previously known is based on optical spectral analysis, such as that which is revealed and described in patent publication U.S. Pat. No. 4,557,603.

Patent publication U.S. Pat. No. 5,973,326 reveals a gas analysis arrangement during the use of a means of emitting infra-red light, located within a chamber, and where the inner surface of this chamber has been assigned properties with high reflectance for light.

In particular, there is revealed here that the light-emitting means is reflected from elliptical or ellipsoidal surfaces and intermediate plane surfaces, in order in this way to be able to focus onto a light-receiving means.

It will be possible also in this case for light radiation formed within the chamber to be absorbed by the gas, contained within the said chamber, in a manner related to frequency, and where a comparison based on frequency between the intensity of the light-emitting means and the intensity related to frequency detected in the light-receiving means creates the conditions required in order to be able to detect not only the occurrence of a gas and/or mixture of gases, but also to measure the current gas concentration.

If the features associated with the present invention and the measures that are required in order to be able to offer rapid reaction times for a gas analysis arrangement of the type described here are considered, then it is true that taking several measures in order to reduce reaction times for the gas analysis are previously known.

Thus it is previously known, in order to increase the sensitivity of a gas analysis arrangement and in order to reduce its reaction time, that it is possible to create the conditions required with the aid of separately driven equipment arranged at the side such that a gas fraction for analysis can be pumped out from a main flow and allowing gas fraction after gas fraction to pass with a selected speed through the chamber that is used for the actual measurement.

It is also previously known to allow the application of the chamber for a gas analysis arrangement in a main flow, whereby the speed of the main flow will determine the reaction time obtained.

The use of various pieces of equipment and means to press a gas or a gas mixture through a chamber within a gas analysis system leads to such systems being denoted as "active" systems.

Gas analysis systems are also known in which the fraction of gas or mixture of gases intended for analysis is allowed, via diffusion, to pass into the chamber. Such a system is denoted as a "passive" system.

With the embodiments of gas analysis arrangements with the features described in the introduction and that as illustrated by the patent publication referred to above, WO 93/11418, it is clear that the small holes formed and distributed along lines in this case will give a very slow diffusion, and that in this way such a gas analysis arrangement will only be able to evaluate delayed, slowly changing average values. The reaction time will, in this way, be very long.

Systems reflecting a light beam also belong to the prior art, as specified in FIG. 8 in the following description, in which the light-emitting means produces a divergent light beam or light cone, and where such a light beam is allowed to reflect from a concave surface, and where the light beam in this way converges towards a receiving means for the light beam, in order to create in this means a strong (intense) image of the light-emitting means.

If the conditions associated with the present invention are considered, it can be seen that for a reflection pattern according to FIG. 8, an undesirable focussed image of the light source is formed at the detector, while the invention aims at being based on the conditions required in order to form an image in the detector of the light source, which, while being in focus, remains diffuse.

DESCRIPTION OF THE PRESENT INVENTION

Technical Problems

If the situation is considered that the technical evaluations that one skilled in the arts must carry out within the relevant technical field or area in order to be able to offer a solution to one or several of the technical problems that are posed, are not only an initial necessary insight into the steps or measures and/or the sequence of steps or measures that are to be taken, but also a necessary choice of the means (singular or plural) that are required, then the following technical problems should be, with respect to this, relevant during the development of the present invention.

When considering the prior art, therefore, such as that which has been described above and particularly in association with the International patent publication WO 93/11481, the ability to realise the significance of, and the advantages associated with, creating through simple means the conditions required such that a shorter reaction time can in this way be offered, even when the gas analysis system is used within different applications where the conditions according to Category "A" or "passive" systems are fully, or at least to a significant degree, present, should be seen as a technical problem.

Thus there lies a technical problem in the ability to realise the significance of, and the advantages associated with, creating the conditions required, for a gas analysis system of the type considered here and when using the concept of a waveguide, which will offer an intense optical signal that, despite this, is a diffuse object, without requiring the use of lenses, where no detector is required that depends on a sharply focussed image of the light source, something that in turn means modest or no requirements for alignment, which in turn provides robust stability with respect to heat, impacts, vibrations and similar, with long calibration intervals, which thus makes it in practice free of maintenance, such that it will be possible to evaluate the light intensity related to frequency in the receiving means for reflected light as a function of frequency, and with a large aperture, or several large apertures, assigned to the chamber, in order in this way to be able to offer the conditions required for a very rapid diffusion capacity of the gas or mixture of gases in the immediate surroundings into and out from the chamber for the formation of a measurement volume.

A technical problem lies in the ability to realise the significance of, and the advantages associated with, creating in a simple manner the conditions within the chamber required such that a spectral analysis related to frequency can take place with the aid of complete and continuous reflecting surfaces within the chamber, between the light-emitting means and the means of receiving reflected light.

A technical problem lies in the ability to realise the significance of, and the advantages associated with, creating within a chamber the conditions required such that it will be possible to make the diffusion time related to the chamber shorter, and this with the aid of an aperture, oriented along a well-defined section of surface that is oriented parallel, or at least essentially parallel, to the direction of propagation of the light beam.

Thus there lies a technical problem in the ability to realise the significance of, and the advantages associated with, allowing the said chamber to be assigned a somewhat curved design, between the said light-emitting means and the means of receiving reflected light, and where a surface with a concave form assigned to the chamber, which is the same as the side surfaces assigned to the chamber, forms all or essentially all of the light-reflecting surfaces that are required, while an aperture assigned to the chamber is to be oriented opposite to the said concave surface.

Thus these lies a technical problem in the ability to realise the significance of, and the advantages associated with, allowing the said light-emitting means and the said means of receiving reflected light to be located at the ends of the concave surface within the chamber that is used.

A technical problem also lies in the ability to realise the significance of, and the advantages associated with, allowing the said aperture or apertures to be oriented in a single narrow extent, between the said light-emitting means and the said light-receiving means.

A technical problem also lies in the ability to realise the significance of, and the advantages associated with, allowing the said aperture to be assigned a size and an extent and an orientation that will offer a rapid "passive" exchange, primarily through diffusion, of a complete sample of gas within the chamber for another complete sample of gas.

Thus there lies a technical problem in the ability to realise the significance of, and the advantages associated with, allowing the total surface area of the said aperture and/or apertures to be adapted in a co-ordinated manner to cover more than 15% of the total inner surface of the chamber, located between the light-emitting means and the light-receiving means.

A technical problem also lies in the ability to realise the significance of, and the advantages associated with, allowing the total surface area of the said aperture to be adapted in a coordinated manner to cover less than 50% of the total inner surface of the chamber, located between the light-emitting means and the light-receiving means.

Thus there lies a technical problem in the ability to realise the significance of, and the advantages associated with, allowing the total surface area of the said aperture to be adapted to cover 20-30% of the total inner surface of the chamber, located between the light-emitting means and the light-receiving means.

A technical problem also lies in the ability to realise the significance of, and the advantages associated with, allowing the said aperture to be assigned to one of four sides that are assigned to a square or equivalent form.

A technical problem also lies in the ability to realise the significance of, and the advantages associated with, when using a light-emitting means that offers a large angle of divergence for a diverging light beam or light cone, creating the conditions required such that it will be possible to select a radius of curvature assigned to the chamber that is smaller than that selected for a light-emitting means that offers a narrow angle of divergence for its divergent light beam.

A technical problem also lies in the ability to realise the significance of, and the advantages associated with, allowing, for a light-emitting means that offers a large angle of divergence for its diverging light beam or light cone a radius of curvature assigned to the chamber for the concave curved surface to be selected that is smaller relative to the distance between the light-emitting means and the surface of the chamber than when using a light-emitting means that offers a narrow angle of divergence for its diverging light beam.

Thus, there lies a technical problem in the ability to realise the significance of, and the advantages associated with, creating the conditions required such that a single, or at least a small number of, filters can be adapted to cover the aperture adapted for the chamber.

Furthermore, the ability to realise the significance of, and the advantages associated with, allowing a central line assigned to the light beam to connect to a direction of a tangent, oriented through the concave curved surface and that section of surface that is located next to the light-emitting means should be seen as a technical problem.

Furthermore, the ability to realise the significance of, and the advantages associated with, allowing a central line assigned to the light beam to be assigned a low or a small angle relative to the said tangent should be seen as a technical problem.

Furthermore, the ability to realise the significance of, and the advantages associated with, and the conditions associated with, creating a strongly focussed cone of light, without posing the requirement for a focussed image of the light-emitting means, is a technical problem.

Furthermore, the ability to create with simple means the conditions required such that it will be possible for the light beam or light cone that is created to be reflected a selected number, while remaining a low number, of times in and along the concave surface should be seen as a technical problem.

The Solution

The present invention is based on the prior art described in the introduction, in which a gas analysis arrangement is to comprise a chamber, containing a gas sample, light-emitting means, means for receiving light that has been reflected through the chamber, and an electronic circuit, adapted such that it is able, by means of spectral analysis, to analyse and determine the presence of and/or the concentration of a selected gas and/or mixture of gases, present as a sample of gas within the said chamber.

The invention is based on opposite and second surfaces within the chamber offering excellent light-reflecting properties, and the said chamber offering one or more apertures, for the passage by diffusion of the gas into and out of the said chamber.

In particular, the invention is based upon the said chamber being assigned a form in which it is to be possible to locate the said aperture and/or apertures within, and to define the limitations of, the chamber, between the said light-emitting means and the said light-receiving means.

In order to be able to solve one or several of the technical problems specified above, the present invention now proposes in particular allowing the said chamber, and/or one reflecting surface of it, to be assigned a somewhat concave curved shape, between the said light-emitting means and the said light-receiving means, and that the said aperture and/or apertures are to be located in a single well-defined extent between the said light-emitting means and the said light-receiving means and that the said aperture is assigned a size and an extent that offer rapid exchange of one gas sample by another gas sample, either passively or actively, and principally by the action of diffusion.

As preferred embodiments, falling within the framework of the fundamental idea of the present invention, it is proposed that the said light-emitting means and the said light-receiving means are to be located at the ends of the said chamber and/or the said curved light-reflecting surface.

Furthermore, it is proposed that the total surface area of the said aperture and/or the said apertures is to be adapted in a coordinated manner such that it covers more than 15% of the total inner surface area of the chamber, between the light-emitting means and the light-receiving means.

Furthermore, it is proposed that the total surface area of the said aperture is to be adapted in a co-ordinated manner such that it covers less than 50% of the total inner surface area of the chamber, between the light-emitting means and the light-receiving means.

In particular, it is proposed that the total surface area of the said aperture is to be adapted such that it covers 20-30% of the total inner surface area of the chamber, between the light-emitting means and the light-receiving means.

Furthermore, it is proposed that it is to be possible to assign a square, or at least essentially square, cross-section to the said aperture.

It is an advantage if the said aperture can be assigned to one of four sides assigned to a square or equivalent.

Furthermore, the invention proposes that the radius of curvature assigned to the chamber and/or the curved light-reflecting surface is to be selected at a light-emitting means that offers a large angle of divergence for a divergent light beam or cone of light, to be less than at a light-emitting means offering a small angle of divergence for a divergent light beam.

For a light-emitting means, offering a large angle of divergence for a divergent light beam, the radius of curvature assigned to the chamber and/or the curved light-reflecting surface is to be selected to be less relative to the distance of the light-emitting means from the surface of the chamber than for a light-emitting means offering a small angle of divergence for a light beam the diverges only to a small extent.

Furthermore, it is proposed that it is an advantage that a single filter is adapted to cover a single aperture.

Furthermore, it is proposed that the central line or ray assigned to the light beam is to be adapted to join onto the direction of a tangent through the concave curved light-reflecting surface and the section of surface that is located next to the light-emitting means.

The central line assigned to the light beam is to be assigned a low angle relative to the said tangent.

In particular, it must be possible to assign to the central line assigned to the light beam an angular value within 10° relative to the said tangent.

In the said means for receiving reflected light, a strongly focussed light beam or light cone arises, without forming, however, a direct image of the light-emitting means.

The light beam or light cone produced in the light-emitting means, such as its central beam, is adapted to be reflected a selected number of times, being a low number, in the concave surface before it impinges on the light-receiving means, where the number of reflections of the central ray is selected to be less than eight, such as a number selected to lie between three and five.

Advantages

The advantages that can be principally regarded as characteristic for the present invention and the special significant characteristics that are in this way proposed are that in this manner the conditions have been created that are required in order to be able to offer a gas analysis system with a specially designed chamber, in order to be able to contain a gas sample intended for analysis, adapted for a suitable application within passive systems.

The diffusion of the surrounding gas or mixture of gases into the chamber may occur at a rapid rate through one or a small number of large apertures into the chamber.

The chamber is assigned a somewhat curved shape in order in this way to form a concave light-reflecting surface, located between the light-emitting means and the means for receiving reflected light.

A strongly focussed light beam or light cone is presented to the means of receiving reflected light via reflections along the concave surface, without the requirement for a focussed image of the light-emitting means, and the number of reflections in the curved light-reflecting surface is selected such that the image does not give any noticeable changes that depend on time.

The means for receiving reflected light is connected to an electronic circuit that is adapted such that it is able, through spectral analysis, to evaluate the presence of a selected gas or mixture of gases and/or the concentration of the contained gas or mixture of gases, and to provide when the value becomes too high an optical or audible signal to an alarm unit.

That which can be considered to be characteristic for an arrangement according to the present invention is specified in the characterising part of the attached patent claim 1.

BRIEF DESCRIPTION OF THE DRAWINGS

A currently suggested embodiment of an arrangement demonstrating the significant features associated with the present invention will now be described in more detail for the purposes of exemplification with reference to the attached drawings, where:

FIG. 6 shows the first embodiment, according to FIG. 3, from below and with a filter having been removed, FIG. 7 shows the first embodiment, according to FIG. 3, from below and with a filter having been removed, and having an alternative design of a shaped aperture to that shown in FIG. 6, FIG. 8 is intended to illustrate the prior art, in which a light-emitting means is adapted to project a light beam or light cone onto a concave mirror surface with the form of an arc of a circle, and where the focussed image of the light-emitting means arises, having a high intensity of light, in a means of receiving reflected light, FIG. 9 is intended to illustrate a practical borderline case, according to the present invention, in which a light-emitting means is adapted to project a light beam or a light cone onto a concave mirror surface with the form of an arc of a circle and where the somewhat diffuse image of the light-emitting means will arise with a high intensity of light in a means of receiving reflected light, while using, in principle, only two reflection surfaces or reflection points.

DESCRIPTION OF THE PRIOR ART

Figure 1:
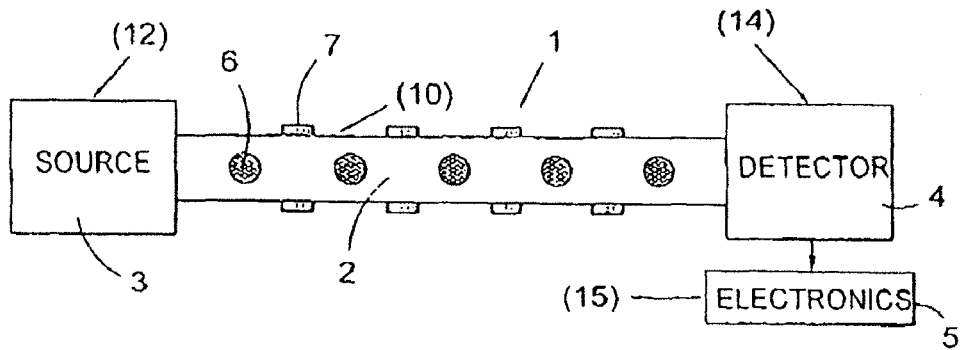
FIG. 1 shows the prior art according to FIG. 1 of the International patent publication WO 93/11418.

With reference to FIG. 1, a previously known embodiment of a gas analysis arrangement is shown, from which arrangement the present invention can be regarded as a development.

Reference is made to the contents of the International patent publication WO 93/11481 for a more detailed description of the arrangement according to FIG. 1.

However, it can here be pointed out that the gas analysis arrangement 1 comprises a chamber 2, containing a gas sample, light-emitting means 3, a means 4 of receiving light reflected through the chamber 2 and an electronic circuit adapted such that it is able using frequency analysis to, in a known manner, analyse and determine the presence of and the concentration of a selected gas and/or mixture of gases present in the said chamber 2.

Four inwardly facing surfaces within the said chamber offer light-reflecting properties, in a manner that is known. It should, however, be pointed out that the light-reflecting properties will be limited by the designed apertures.

The said chamber 2 offers a small number of apertures, located in four lines each along one of the four sides, structured as pairs of apertures 6 with circular shape, and as perpendicular pairs of apertures 7 with circular shape, where these apertures are adapted in order to offer passage for a gas sample into and out of the said chamber via diffusion.

The said chamber 2 is furthermore assigned a long and narrow shape, and the said apertures having the shape of a circle are located within the chamber, between the said light-emitting means 3 and the said light-receiving means 4.

The total surface area of the apertures is adapted to comprise approximately 10% of the total outer surface of the chamber, and it can in this way be assumed to provide an equivalent reduction in the intensity of light received by the means 4.

DESCRIPTION OF THE EMBODIMENT SUGGESTED

It should initially be made clear that we have selected terms and a special terminology in the subsequent description of an embodiment suggested at the present time that demonstrates the significant characteristics associated with the invention and that is described in the drawings shown in the attached figures, in order, primarily, to make clear the innovative concept of the invention.

It should, however, be taken into consideration in this context that the expressions selected here are not to be seen as limiting to only the term selected and used, but it is rather to be understood that each such selected term is to be interpreted such that it additionally covers all technical equivalents that act in the same manner, or in essentially the same manner, in order in this way to achieve the same intention and/or technical result, or essentially the same intention and/or technical result.

Figure 2:
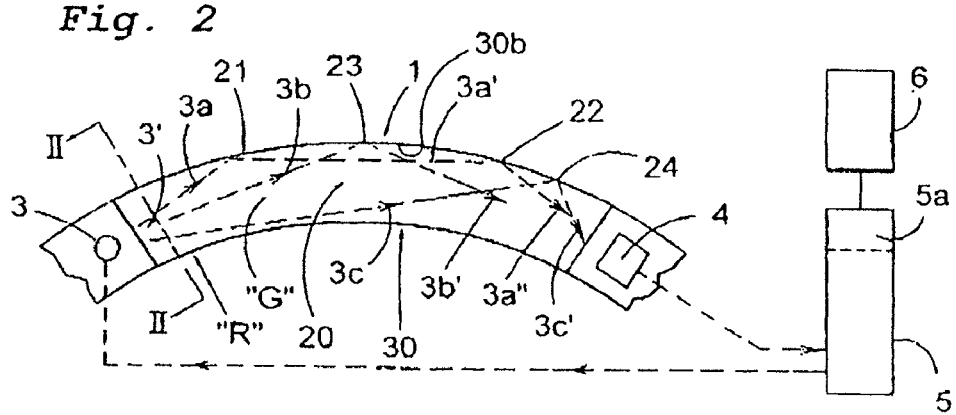
FIG. 2 shows a side view and a section of a first embodiment of a gas analysis arrangement according to the present invention.

With reference to FIG. 2, there is schematically shown the basic preconditions for the present invention, and where the significant characteristics associated with the invention with respect to the shape of the chamber, the location of the light-emitting means and the location of the means of receiving reflected light, are generally made clear through the proposed embodiments that will subsequently be described in more detail.

Thus FIG. 2 illustrates a gas analysis arrangement 1 with a construction that is, in principle, equivalent to that shown in FIG. 1 and where equivalent components have therefore been assigned equivalent reference numerals.

The gas analysis system 1 comprises a chamber 20, containing a gas sample, a light-emitting means 3, a means 4 of receiving light reflected through the chamber 20, and an electronic circuit 5, adapted such that it is able, by means of spectral analysis, to analyse and determine the presence of and the concentration of a selected gas and/or mixture of gases, present as a gas sample "G" within the said chamber 20.

The electronic circuit 5 may also comprise a simple comparator, in order to carry out in the comparator an electronic comparison of the instantaneous value and a stored limit value such that an optical or an acoustic circuit is activated when the determined instantaneous value exceeds the stored limit value.

The embodiment according to FIG. 2 illustrates for the purposes of simplification the removal of a section of a wall belonging to the chamber, facing the reader, in order in this way to be able to illustrate the beam or ray path.

The calculating electronic circuit 5 also comprises, according to FIG. 2, a table 5a, in which a number of selected limit values for a selected gas and/or mixture of gases are stored, together with a comparator circuit, such that an alarm circuit 6, optical or acoustic, is activated in a known manner when the instantaneous value for a selected gas and/or mixture of gases, within the calculating circuit 5, exceeds a limiting value stored in the table.

Figure 3:
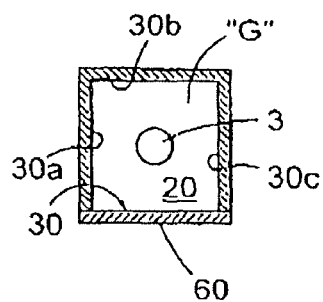
FIG. 3 shows a first embodiment of a selected cross-section for a chamber used.
Figure 4:
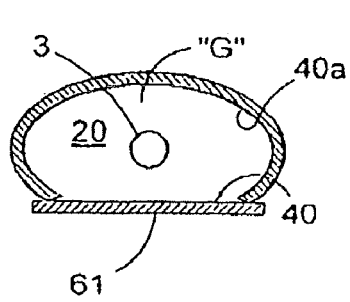
FIG. 4 shows a second embodiment of a selected cross-section for a chamber used.
Figure 5:
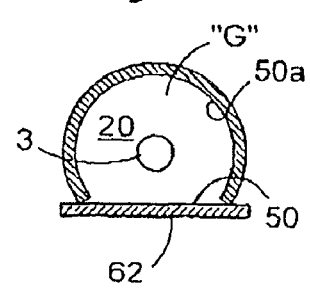
FIG. 5 shows a third embodiment of a selected cross-section for a chamber used.

Three different embodiments of the selected cross-section of the chamber 20 are shown in FIGS. 3, 4 and 5, where FIG. 3 illustrates a more square cross-section next to the light-emitting means 3, FIG. 4 illustrates a part of an elliptical cross-section, and FIG. 5 illustrates a part of a circular cross-section.

The following is valid for the embodiment according to FIG. 3 the surfaces 30a, 30b and 30c, of which surfaces 30a and 30c are directly opposite to each other and oriented parallel to each other, offer extremely highly light-reflecting properties.

With respect to FIG. 4, the partially ellipsoidal surface 40a offers light-reflecting properties, and with respect to FIG. 5, the partially toroidal surface 50a offers light-reflecting properties.

Each one of these embodiments comprises at least one aperture 30, 40 and 50, in order in this way to allow a sample "G" of gas to be able rapidly to pass into and out from the said chamber 20, where exchange of gas will take place via a pronounced diffusion.

The chamber 20 may, as is the case in the embodiment according to FIG. 1, be assigned a long and narrow structure with the said apertures 30, 40 and 50 replacing a part or section of a wall, forming the chamber 20, where these apertures extend continuously and directly between the said light-emitting means 3 and the said light-receiving means 4.

FIGS. 3, 4 and 5 are to be considered as illustrating the cross-section of the chamber 20 taken across the section "II-II" in FIG. 2, in the close vicinity of the light-emitting means 3.

Although FIG. 2 shows a side view where the chamber 20 consists of two opposite surfaces 30*a*, 30*c* curved to form part of a circular ring and a partially cylindrical surface 30*b*, it is clear that curved surfaces other than these can be used.

Thus, curves that connect to or are constituted by partial ellipses can be selected instead of those shaped as a part of a circular ring.

Since the invention is built upon a more or less diffuse image of the light-transmitting means 3 appearing at the light-receiving means 4, the possibility of assigning different curvatures and different radii of curvature to is the curved light-reflecting surface 30*b* lies within the selected embodiment.

With renewed reference to FIG. 2, it is thus illustrated that the said chamber 20 has been assigned a continuous, somewhat curved, shape, between the said light-emitting means 3 and the said light-receiving means 4, here illustrated in the form of a partially circular curvature, the radius of which has been given the reference symbol "R".

Not only curvatures that are part of a circular arc, cylindrical curvatures and elliptical curvatures fall within the framework of the invention, other curvatures that it would be possible to adapt in order for it to be possible to allow in the manner proposed by the invention emitted light 3 in the form of a divergent light beam or light cone 3' to pass through the chamber 20 to as great an extent as possible in order to be collected after convergence in the light-receiving means 4 within its lobe of reception also fall within its frame-work.

FIG. 2 thus illustrates more exactly, for the purposes of clarification, that the light-emitting means 3 can be considered to produce a somewhat diverging (say 15°) light beam, the central beam or ray 3*a* of which is directed towards a point 21 and is there reflected to a light ray 3*a*' that is directed closer to the horizontal and which in turn is reflected, in a second point 22, as a light ray 3*a*" towards and to be received by the means 4.

The means 3 can be adjusted such that another light ray 3*b* can be reflected at a point 23 and transferred as a light ray 3*c*' to the means 4. A further light ray 3*c* from the means 3 is shown reflected at a point 24, in order to be subsequently reflected to the means 4 as a light ray 3*c*'.

Directly acting light rays can also, to a restricted amount, be used in this case.

With reference to FIG. 6, it is illustrated that the emitted light beam 3', with its light ray 3*d*, can be allowed to reflect in the parallel and plane sections of wall 30*c* and 30*a*, and again on the section of wall 30*c* before the light ray 3*d*' is detected by the light-receiving means 4.

The basic idea of the invention is based upon shaped apertures 30, 40, 50, preferably one single aperture, according to FIG. 7, although a number of apertures, where the number is a small number, are to be located in a single and extended extent between the said light-emitting means 3 and the said light-receiving means 4 and that the said aperture is to be assigned a size and an extent that will have the ability to offer a rapid passive diffusion for an exchange of one sample of gas "G" within the chamber 20 for another, and where it will be possible to adapt as required the rate of the exchange of a sample of gas within the chamber for another sample.

The free exposure of the chamber 20 that is offered by the invention by allowing the removal of a section of a wall for the chamber 20 suggests that it should be possible to reduce the speed and time of diffusion to less than one second, and preferably also to less than 0.5 seconds.

With reference to FIG. 7, it is there illustrated that the aperture has been divided into two parts 30*a* and 30*b* with a section 31 that is located between them and that covers the chamber, the surface section 31*a* of which that faces the chamber 20 may offer highly reflective properties.

The total surface area of the said aperture 30, 40, or 50 and/or the apertures 30*a*, 30*b* is adapted in a co-ordinated manner such that it will be possible to cover at least in excess of 15-25% of the total inner surface of the chamber 20 between the light-emitting means 3 and the light-receiving means 4.

In particular, it is proposed that the total surface area of the aperture 30, 40 or 50, or of 30*a*, 30*b*, is to be adapted in a co-ordinated manner to cover at least less than 50% of the total inner surface of the chamber, between the light-emitting means 3 and the light-receiving means 4, in order in this way to liberate reflecting surface sections and in particular the curved surface section 30*b*.

Figure 10:
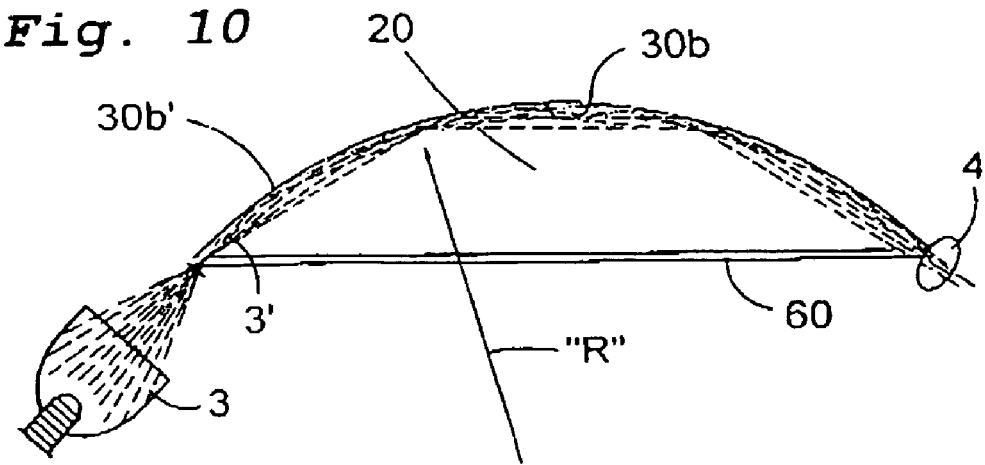
FIG. 10 is intended to illustrate a more suitable case, according to the present invention, in which a light-emitting means is adapted to project with a small angle of incidence a light beam or light cone onto a concave mirror surface with the form of an arc of a circle, and where the further diffuse image of the light-emitting means will arise with a high intensity in a means of receiving reflected light, while using, in principle, four or five reflection surfaces or reflection points.

The total surface area of the said aperture 30, 40 or 50 is, in particular, adapted in order to cover 20-30% of the total inner surface of the chamber 20 between the light-emitting means 3 and the light-receiving means 4, where FIG. 10 suggests a relationship that lies around 25%.

The embodiments according to FIGS. 3, 4, 5, 6, 7, 10 and 12 allow the illustration of the assignment to the said aperture of a square, or essentially square, cross-section, but it should be taken into consideration that other forms of the size and shape of the aperture fall within the framework of the invention, anything for the purpose of being able to reduce the reaction time for a gas analysis system 1 according to the invention, and in this way increase the rate of diffusion, preferably by the use of the "active" heat that is produced by the light-emitting means 3.

FIG. 3 illustrates that the said aperture 30 is assigned one complete side of the four sides of a square.

FIG. 4 illustrates that the said aperture 40 is assigned one part of a curved ellipsoidal surface where this part has been selected to have a width that is less than one half of the major diameter.

FIG. 5 illustrates that the said aperture 50 is assigned one part of a toroidal or cylindrical surface with a width that is less than the diameter.

The radius of curvature "R" assigned to the chamber 20 is selected at a light-emitting means 3 that offers a large angle of divergence for the diverging light beam 3', with central rays having been assigned reference numerals 3*a*, 3*b*, 3*c* and 3*d*, to be less at a distance means from the inner surface 30*b* of the chamber than it is for a light-emitting means 3 offering a small angle of divergence for diverging rays within the light beam 3'.

Said distance is illustrated in FIG. 3, and other figures, with the reference symbol "a".

A filter 60 is adapted to cover the aperture 30 in the embodiment according to FIG. 3, a filter 61 is adapted to cover the aperture 40 in the embodiment according to FIG. 4, and a filter 62 is adapted to cover the aperture 50 in the embodiment according to FIG. 5.

Filters of the type used here are well-known and will not be described in detail.

In particular, the present invention proposes that the filter surface used is to be adapted such that it is able to cover the said aperture 30, 40 or 50 with a factor of 10-25 (1/mm) relative to the volume enclosed by the chamber 20.

Figure 12:
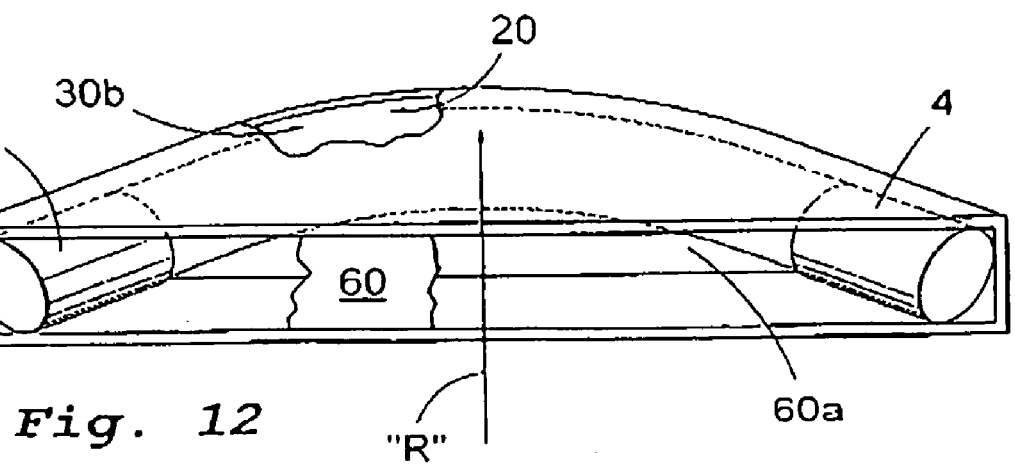
FIG. 12 shows a perspective view of an alternative to the embodiment according to FIGS. 2 and 3.

The said light-emitting means 3 and the said light-receiving means 4 are in all embodiments located at the ends of the said chamber 20 as it has been defined, but there is nothing to prevent allowing the sections of surface of the surfaces that form the chamber 20 to extend beyond the definition of the chamber 20, in order to attach the light-emitting means 3 an light-receiving means 4 in the extensions, according to the embodiment shown in FIG. 12.

There is nothing to prevent the introduction into the embodiment according to FIG. 12 of a filter 60a instead of the filter 60 in order in this way to reduce the volume of the chamber 20.

FIG. 8 is intended to illustrate the beam or ray path from a means 3 when its light beam 3' is reflected only once in a surface 30b with the shape of an arc of a circle.

The prior art is illustrated here, in which the light-emitting means 3 is adapted to project a light beam or a light cone 3' onto the concave mirror surface 30b and where the focussed image of the light-emitting means arises with high intensity in a means 4 for receiving reflected light.

FIG. 9 is intended to show a first borderline case, according to the present invention, where a light-emitting means 3 is adapted to project a light beam or light cone 3' onto a concave mirror surface 30b and where the somewhat diffuse image of the light-emitting means 3 arises with a high intensity in a means 4 for receiving reflected light, and with, in principle reflection surfaces or reflection points along the surface 30b.

The focus of the received image may, even in this embodiment, be too sharp for the image to be used to any advantage according to the principles of the invention.

The focus becomes poorer for a higher number of reflections that are used, and practical experience suggests that the number of reflection points for the central ray should be selected to be four or approximately four.

It has been discovered in this case that a central light beam or ray 3a, assigned to the light beam 3', (extended in FIG. 9 through the mirror surface 30b) has been adapted to form a small angle "b" with a tangent line 9 of the curved surface 30b next to the means 3.

In particular, it is a question of a central line or ray 3a assigned to the light beam 3' being adapted to connect to or align with the direction of a tangent line 9, oriented through a curved concave reflecting surface 30b and the surface section 30b' that is located next to the light-emitting means 3.

The central line 3a assigned to the light beam is assigned a small upwards or downwards angle relative to the said tangent line 9, having, however, a value of angle that is normally within 10° relative to the line.

A strongly focussed light beam or light cone arises in both FIG. 9 and FIG. 10 in the said means 4 of receiving reflected light without any direct and focussed image of the light-emitting means 3.

One ray of the light beam 3' or light cone produced by the light-emitting means, such as its central ray 3a, is adapted to be reflected a few times in the concave surface 30b before it reaches the light-receiving means 4.

The number of reflections of the central beam or ray is to be selected in practice to less than eight, such as only two as in FIG. 9, while the number can be selected to between three and five, such as four as in FIG. 10.

It is probable that the embodiment according to FIG. 10 is to be preferred for practical application since the number of reflection points for the central beam or ray 3a can be easily controlled by a changing of the angle of incidence "b" of the central beam or ray 3a onto, and its distance "a" from, the curved surface 30b.

Figure 11:
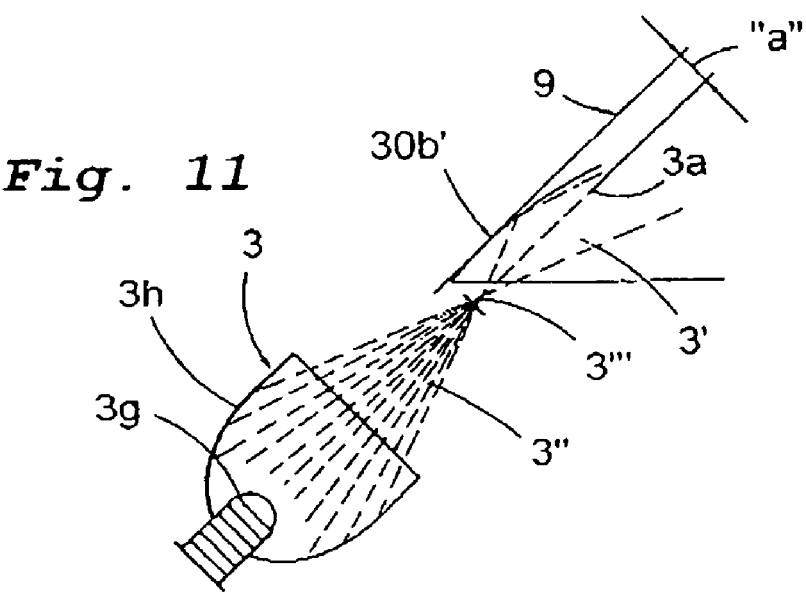
FIG. 11 shows an enlarged detail of the embodiment according to FIG. 10, from which location of the light-emitting means next to the end section of the reflecting concave having the form of an arc of a circle is made clear.

FIGS. 10 and 11 are intended to illustrate a special case, according to the present invention, where the light-emitting means 3 is adapted to project, under a small angle of incidence, the value of the angle "b" being equal to zero according to the definition given in FIG. 9, a light beam or light cone 3' onto a concave mirror surface 30b and where the diffuse image of the light-emitting means 3 arises with a high intensity in a means 4 for receiving reflected light and with, in principle, four or five reflection surfaces or reflection points for the central light beam or ray.

FIG. 11 shows an enlarged drawing of the location of the light-emitting means next to one end section 30b' in FIG. 10 of the reflecting concave surface 30b.

It is shown that the central light beam or ray 3a is parallel to the tangent line 9, and it is dear from this drawing that the angle "b" can be changed to have positive and negative values, where FIG. 9 shows value.

FIG. 11 also illustrates that it will be possible to change the distance "a" with different results for light reception in the means 4.

There is nothing to prevent the application of the same principles as those described above with respect to the locations and directions of the light-emitting means and of the light-receiving means with respect to its light-receiving lobe.

The practical application of the chamber 20 and the image that is received by the means 4 thus can be changed by the following factors:

a. the distance "a" selected,
b. the angular value "b" selected,
c. the form and intensity of the light source, and its angle of divergence (approximately 15°),
d. the position of the means 4 of receiving reflected light and its angle of reception (approximately 15°),
e. the radius "R" of curvature or the curvature selected of the concave surface 30b for reflecting light,
f. the size and location selected of the aperture 30 for extensive diffusion of the sample "G" of gas,
g. the location of the chamber 20 such that heat from the light-emitting means 3 will contribute with a convection flow through the chamber 20.

FIG. 12 shows a perspective view of an alternative to the embodiments according to FIG. 2 and FIG. 3 with a surface wave-guide system, where the means 3 and 4 are located at the ends or located between two parallel surface sections, separated each by a chord.

A filter 60 interacts with these chords, and the reflecting concave surface 30b is extended somewhat outside of the relevant measurement distance in order to interact with and to fix the means 3 and the means 4.

The means 3 can, as is shown in FIG. 11, consist of a filament 3g, a light system 3h in order to converge the light beam 3" to a focal point 3'" and from which the diverging light beam or light cone 3a exits.

The filter 60 can be located further into the chamber 20, shown by the reference numeral 60a, and in this way reduce the volume of the chamber 20 to the volume that FIG. 10 makes clear.

Naturally, the invention is not limited to the embodiments specified above for the purposes of exemplification. It can be modified within the framework of the innovative concept illustrated by the attached claims.

Particular attention should be paid to the fact that each unit can be combined with each other revealed unit within the framework in order to achieve the desired technical function.

The invention claimed is:

1. A gas analysis arrangement comprising:

a chamber adapted to contain a sample of gas, the chamber having first and second opposing ends defining a chamber, wherein at least first and second opposing sides extend between the first and second ends have opposing surface with light reflecting properties within the chamber, a light-emitting means disposed in the first end, a light-receiving means for receiving light that has been reflected through said chamber disposed in the second end opposite the first end, and an electronic circuit adapted by means of spectral analysis to analyze and determine the presence of a selected gas or mixture of gases present as a sample of gas within said chamber, whereby opposite arranged surfaces within the chamber offer light-reflecting properties as a wave guide, wherein said chamber includes one or more apertures for the passage of the gas into and out of said chamber, the chamber has an extended shape, and said one or more apertures are located in the chamber between said light-emitting means and said light-receiving means, wherein the first side of the chamber has a curved shape with its concave surface facing into said chamber, said one or more apertures are located and extended between said light-emitting means and said light-receiving means, and said one or more apertures have a size and a longitudinal extent that allows an exchange of one sample of gas within the chamber for another, wherein said chamber includes said one or more apertures disposed on the second side opposite to said concave surface, said light-emitting means and said means of receiving reflected light are located at the ends of said concave surface, a central line of a light beam is connected to a direction of a tangent oriented through the concave curved surface and a section of the concave curved surface that is located next to the light-emitting means, and wherein all of the one or more apertures are located only on the second side of the chamber.

2. An arrangement according to claim 1, wherein the total surface area of said at least one aperture is adapted in a coordinated manner to cover more than 15% of the total inner surface of the chamber between the light-emitting means and the light-receiving means.

3. An arrangement according to claim 1, wherein the total surface area of said at least one aperture is adapted in a coordinated manner to cover less than 50% of the total inner surface of the chamber between the light-emitting means and the light-receiving means.

4. An arrangement according to claim 1, wherein the total surface area of said at least one aperture is adapted to cover 20-30% of the total inner surface of the chamber between the light-emitting means and the light-receiving means.

5. An arrangement according to claim 1, wherein said at least one aperture has a rectangular, or essentially a rectangular, cross-section.

6. An arrangement according to claim 1, wherein said at least one aperture is located on one of four sides of a square cross-section of the chamber.

7. An arrangement according to claim 1, wherein the central line of the light beam has a small angle relative to said tangent line, and that the angle is 10° or less.

* * * * *